United States Patent
Edwards et al.

(10) Patent No.: US 6,776,968 B2
(45) Date of Patent: Aug. 17, 2004

(54) DIFFUSER

(75) Inventors: Andrew Robert Edwards, Aberdare RCT (GB); Andrew Robert McLeish, Sheffield (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/230,567

(22) Filed: Aug. 29, 2002

(65) Prior Publication Data

US 2003/0044325 A1 Mar. 6, 2003

Related U.S. Application Data

(63) Continuation of application No. PCT/GB01/00837, filed on Feb. 28, 2001.

(30) Foreign Application Priority Data

Feb. 29, 2000 (GB) .............................................. 0004624

(51) Int. Cl.⁷ ................................................ A62B 7/08
(52) U.S. Cl. ....................... 422/126; 422/122; 422/125; D11/131.1
(58) Field of Search ................................ 422/126, 125, 422/122, 4, 5; D11/131.1

(56) References Cited

U.S. PATENT DOCUMENTS

| | | | | |
|---|---|---|---|---|
| 1,530,103 A | * | 3/1925 | Booth | 422/126 |
| 1,969,756 A | * | 8/1934 | Lowell | 422/124 |
| 4,237,097 A | * | 12/1980 | McDuffie | 422/126 |
| 4,664,312 A | | 5/1987 | Bryson | |
| 4,781,895 A | | 11/1988 | Spector | |
| 5,632,768 A | * | 5/1997 | Shimada | 607/96 |
| 5,827,483 A | | 10/1998 | Fullam | |
| 5,873,370 A | * | 2/1999 | Towle et al. | 131/190 |
| 6,061,950 A | * | 5/2000 | Carey et al. | 43/125 |
| D444,732 S | * | 7/2001 | McLeish et al. | D11/131.1 |
| D445,721 S | * | 7/2001 | McLeish et al. | D11/131.1 |

FOREIGN PATENT DOCUMENTS

| | | |
|---|---|---|
| FR | 2 776 929 A1 | 10/1999 |
| GB | 2 223 679 A | 4/1990 |

* cited by examiner

*Primary Examiner*—Krisanne Jastrzab
(74) *Attorney, Agent, or Firm*—Akin Gump Strauss Hauer & Feld, L.L.P.

(57) ABSTRACT

A diffuser includes a base portion and a lid portion. The diffuser is adapted to allow emanation of vapor from a burning block of combustible material and contains a block receiving portion elevated from a surface of the base portion. The block receiving portion has one or more grooves formed in a top surface of the block receiving portion and extending below the top surface of the block receiving portion. The base portion further includes apertures forming channels extending from within the base portion to an outer surface of the base portion. The lid portion is preferably substantially pyramidal in shape and has an apex at an end remote from the base portion. The lid portion further includes apertures positioned towards the apex. In use, a burning block of combustible material, impregnated with fragrance, is placed on the block receiving portion, and the lid portion is placed over the block. The base and lid apertures, together with the grooves in the block receiving portion, serve to optimize the air flow within the diffuser, thus optimizing emanation of the fragrance from the block.

14 Claims, 3 Drawing Sheets

DIFFUSER

CROSS-REFERENCE TO RELATED APPLICATIONS

This application is a continuation of International Application No. PCT/GB01/00837, filed Feb. 28, 2001, which was published in the English language on Sep. 7, 2001, under International Publication No. WO 01/64257 A1 and the disclosure of which is incorporated herein by reference.

BACKGROUND OF THE INVENTION

This invention relates to a device for allowing diffusion of vapor or smoke into the surroundings of the device, and particularly, but not exclusively, to a device for allowing diffusion of dry smoke produced from a combustible solid. The invention relates particularly to the diffusion of dry smoke from a solid containing within it one or more components which produce a fragrance. Alternatively, the solid could include components which act as insecticides, insect repellents, deodorants, germicidal agents or sanitizing agents. Such a device will be referred to herein as a diffuser.

It is known to use a diffuser to burn incense in order to introduce fragrance into a room. The introduction of fragrance into a room can be a mood enhancer and can also mask unwanted household odors such as those caused by cooking, tobacco, pets, etc.

It is known to burn joss-sticks in order to introduce a particular fragrance into a room. The disadvantage of using joss-sticks is that the operation of burning the joss-stick is relatively untidy and messy in that the ash from the joss-stick will fall onto the surface below the joss-stick, for example, a table or a floor. In addition, the burning life of the joss-stick is relatively short and it is necessary to frequently re-light fresh joss-sticks in order to maintain a particular fragrance within a room.

It is also known to use a diffuser to burn solid blocks of combustible material, incorporating either fragrance or other additives such as insecticides etc. However, known diffusers suffer from problems relating to heat transfer from the diffuser to the surface on which the diffuser is positioned, and inefficient burning of the solid block resulting in suboptimal burning of the solid block. Further, with known diffusers it is common for the ash from the burnt solid block to spill over from the diffuser onto a surface on which the diffuser is positioned.

BRIEF SUMMARY OF THE INVENTION

According to the present invention there is provided a diffuser for enabling diffusion of vapor or smoke produced from a burning solid block containing an additive, the diffuser comprising:

a base portion comprising a top surface;

and a block receiving portion having a top surface and an undersurface, the block receiving portion being raised up from the top surface of the base portion to form a platform shaped to receive the block, and comprising one or more grooves on the top surface of the block receiving portion.

While the invention relates to a diffuser for emanating any type of vapor, wet or dry, preferably the vapor comprises a smoke.

The base portion of the diffuser serves to provide a stable base for the block receiving portion. Because the block receiving portion is raised up from the upper surface of the base portion in the form of a platform, it is easily accessible by a person placing the block on the base portion. Because the base is shaped to receive the block, the block is stable within the block receiving portion and is unlikely to topple over.

In use, a block, typically in the shape of a cone, will be positioned on the block receiving portion and the grooves will form channels positioned underneath the block, thus allowing a flow of air to the undersurface of the block. This increases the efficiency of the burning of the block.

Conveniently, the undersurface of the block receiving portion is raised up relative to the undersurface of the remainder of the base portion of the diffuser.

This means that in use, the block receiving portion of the base portion will not be in contact with a surface supporting the diffuser. It has been found that in practice the temperature of the block receiving portion of the diffuser can become very high, for example as high as 100° C. If the block receiving portion were to come into contact with the surface supporting the diffuser, then heat transfer would take place between the diffuser and the surface, typically a table. This could cause damage to the table or other surface and could represent a potential fire hazard.

Alternatively, the base portion may comprise a spacer such as a ring formed on its undersurface, preventing the undersurface of the block receiving portion from coming into contact with a supporting surface.

Advantageously, the block receiving portion is positioned within a depressed portion of the base portion of the diffuser, known as a basin. In other words, the base portion of the diffuser comprises walls which extend above the top surface of the block receiving portion. In use, ash from the burning block will fall into the basin and not onto a supporting surface, such as a table.

Advantageously, the walls of the base portion contain one or more apertures which extend from an inner surface of the walls to an outer surface of the walls, thus providing one or more channels extending from the depressed area to the outside surface of the base portion of the diffuser, through which channels air may pass.

It has been found that the presence of the one or more apertures forming one or more channels, in conjunction with the grooves formed in the block receiving portion, further enhances the flow of air around and underneath the block and improves the efficiency of the burning of the block.

In embodiments of the invention in which the block receiving portion is positioned in a basin, the fact that the block receiving portion is in the form of a platform is particularly advantageous, because it allows a user to easily position a block within the basin.

Advantageously, the diffuser comprises a lid portion adapted to fit over the base portion of the diffuser. Conveniently, the lid portion is substantially pyramidal in shape, having an apex positioned at an end remote from the base portion of the diffuser.

Preferably, the lid portion comprises one or more apertures positioned towards the apex of the lid portion, which apertures serve, in use, to enhance the flow of air and vapor within the diffuser. The apertures also serve to provide a controlled rate of burning.

Although the size of the apertures will be determined by the dimensions of the device, it has been found that holes of at least 5 mm in diameter are particularly efficient in improving the flow of air around the device. It has also been found, however, that the optimum size of aperture varies with the particular fragrance added to the block.

Instead of having several holes positioned close to the apex of the lid, an alternative embodiment comprises a single hole positioned at the top of the apex.

Advantageously, the block is substantially cone-shaped. It has been found that a block of this shape has particular aesthetic appeal. In addition, because the cross-section at the top of the cone is smaller than at the bottom, it allows for easier lighting of the cone, when a flame is applied to the top of the cone initially.

Alternatively the block could be cylindrical or cuboidal in shape, for example.

Preferably, the block is formed from a mixture of wood pulp, resins which serve as binders, and fillers made of fibrous material, such as coconut husks.

The fibrous material retards burning to ensure that the block burns for approximately 20 minutes in a controlled manner.

The block is impregnated with fragrance, such as incense fragrance. When the block is burning, the fragrance is released into the atmosphere.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
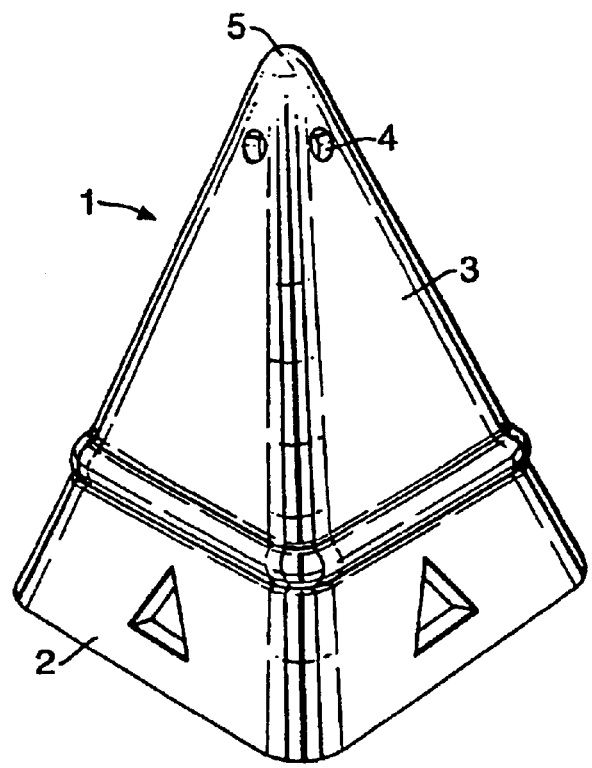
FIG. 1 is a front perspective view from above and one side of a diffuser according to a first embodiment of the invention.

Referring to FIGS. 1 to 4, a diffuser according to a first embodiment of the invention is designated generally by the reference numeral 1. The diffuser 1 comprises a base portion 2 and a lid portion 3. The lid portion 3 is adapted to fit with the base portion 2.

The base portion will now be described with reference particularly to FIGS. 3 and 4. The base portion 2 comprises a block receiving portion 40 which is raised up from a top surface 41 of the base portion 2 to form a platform. Further, the platform or block receiving portion 40 is shaped to receive a block (not shown) formed from a material in which a fragrance has been impregnated. The block may be of any desirable shape, but typically it is cone-shaped. The block is substantially made from wood pulp, which allows the block to burn, and is impregnated with fragrance.

The base portion 2 is shaped to form a basin 44 which basin acts as a container for collecting ash produced when the block is burning.

The base portion 2 provides a stable base for the block receiving portion. In addition, because the block receiving portion 40 is raised up from the upper surface 41 of the base portion 2, it is easily accessible by a person placing the block on the block receiving portion 40.

The block receiving portion 40 comprises one or more grooves 42 which in this example form a cross but could also have any other convenient geometrical shape. The grooves extend below the surface of the block receiving portion 40. In use, the grooves 42 will allow air to pass beneath the block thus allowing a flow of air to the undersurface of the block while it is burning.

Figure 3:
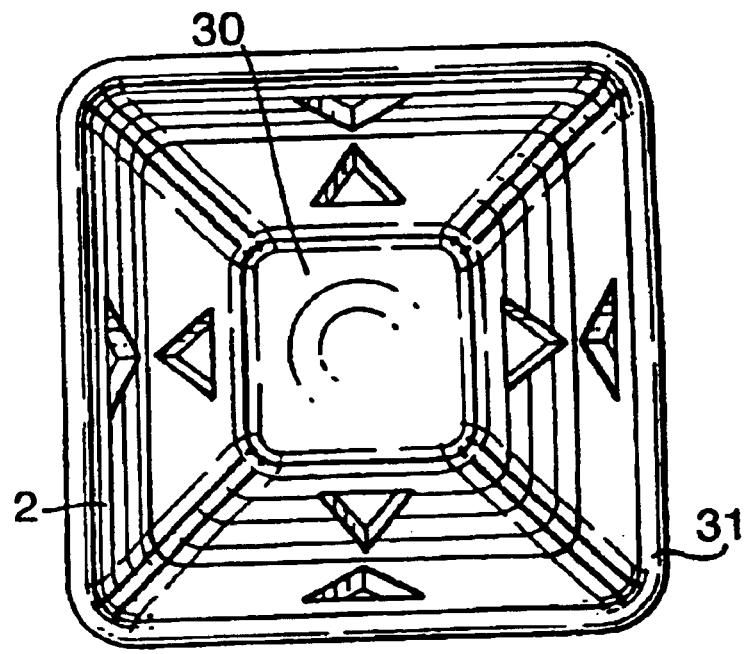
FIG. 3 is an underneath view of the diffuser of FIG. 1.
Figure 4:
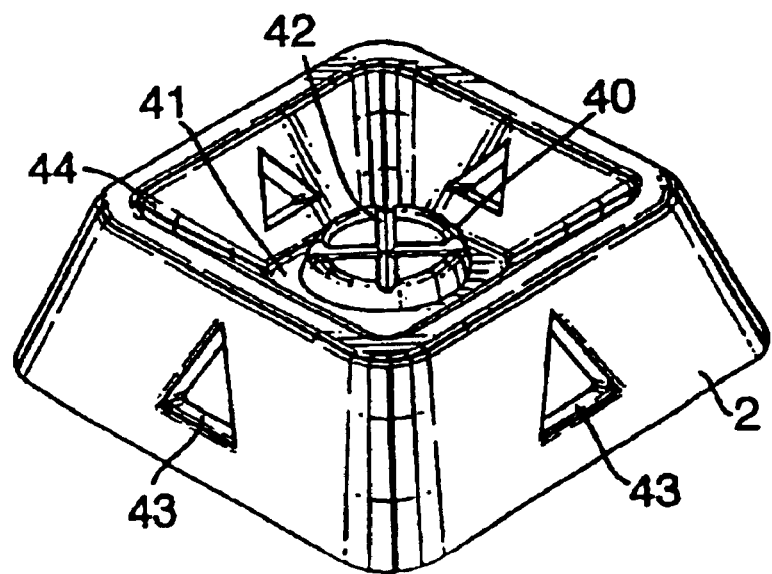
FIG. 4 is a front perspective view from above and one side of the base portion of the diffuser of FIG. 1.

The undersurface 30 of the block receiving portion 40 is raised up relative to the undersurface 31 of the base portion of the diffuser, as shown in FIG. 3. This prevents the block receiving portion 40 from coming into contact with a surface such as a table on which the diffuser has been placed. This prevents damage to the table through transfer of heat from the block receiving portion which will heat up towards the end of the burning cycle of the block.

The base portion is also formed with apertures 43. In this embodiment four apertures are shown each of which is triangular in shape. However any number of apertures could be incorporated into the base portion, each of which could have any desired geometrical shape.

Figure 2:
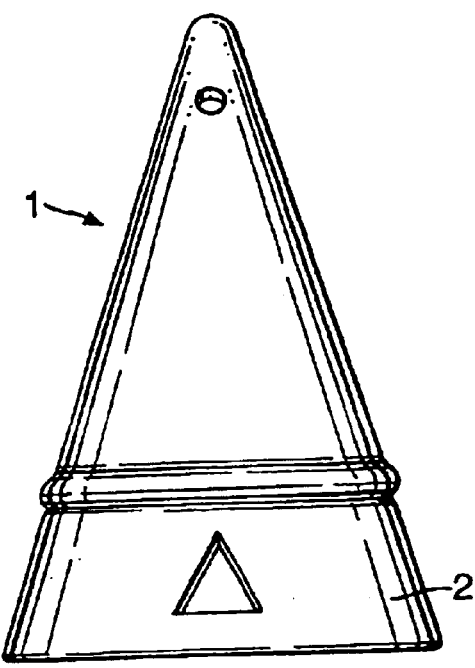
FIG. 2 is a side view of the diffuser of FIG. 1.

The diffuser 1 further comprises a lid portion 3 as shown in FIGS. 1 and 2. The lid portion is substantially pyramidal in shape, and fits with the base portion. When placed on the base portion the diffuser as a whole is substantially pyramidal in shape.

The lid portion 3 comprises apertures 4 positioned towards the apex 5 of the lid portion. In the present embodiment, four apertures 4 are positioned towards the apex 5. However, any other number of apertures could be present of any desired shape. In use, a block will be lit by a user, such that the block burns initially with a flame. The flame will be extinguished by the user to leave a glowing ember, with the block emitting smoke impregnated with fragrance. The block will be placed on the block receiving portion 40 by the user, and the lid portion 3 will then be positioned over the base portion thus covering the block. The apertures 4 in the lid portion 3 and apertures 43 in the base portion 2 together with grooves 42 in the block receiving portion 40 optimize air flow through the diffuser resulting in efficient burning of the block allowing optimum emanation of fragrance.

Figure 5:
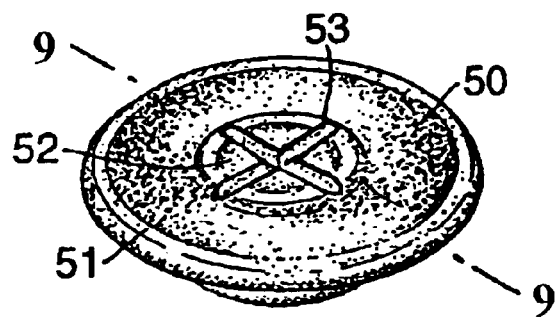
FIG. 5 is a perspective view from above of a diffuser according to a second embodiment of the present invention.
Figure 6:
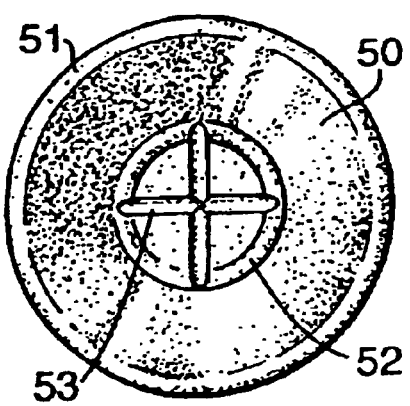
FIG. 6 is a plan view of the diffuser of FIG. 5.
Figure 7:
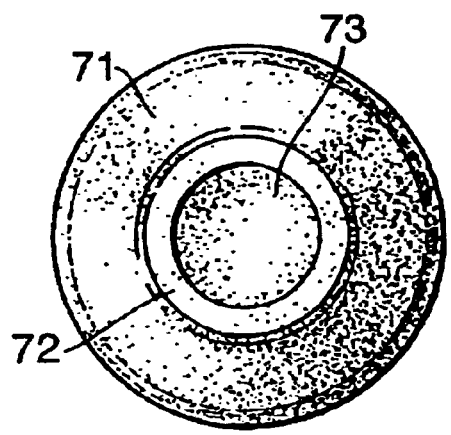
FIG. 7 is a view from below of the diffuser of FIG. 5.
Figure 8:
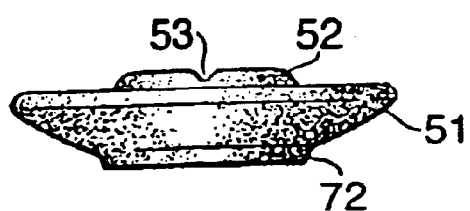
FIG. 8 is a side view of the diffuser of FIG. 5.
Figure 9:
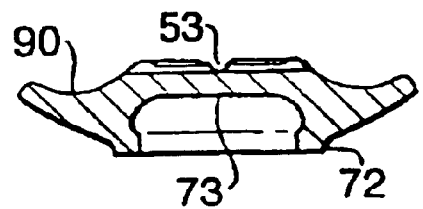
FIG. 9 is a sectional view of the device in the direction of line 9—9 in FIG. 5.

Turning now to FIGS. 5 to 9, a second embodiment of the present invention is shown. The second embodiment comprises a diffuser 50 which is substantially disc-shaped. The diffuser 50 comprises a base portion 51 and a block receiving portion 52. The block receiving portion is similar to block receiving portion 40 shown in FIG. 1 and comprises grooves 53 which are similar to grooves 42 shown in FIG. 4 in respect of the first embodiment of the present invention. The block receiving portion 52, as shown in FIG. 5, is formed as a platform and is shaped to receive a block.

The base portion 51 comprises on an underneath surface 71 a ring 72 extending from the underneath surface 71 of the base portion 51. In use, the ring 72 will come into contact with a surface, such as a table, on which the diffuser 50 is placed. The ring thus acts as a spacer ensuring that an underneath surface 73 of the block receiving portion 52 does not come into contact with a supporting surface, such as a table, thus minimizing any damage which may be caused due to heat transfer from the burning block through the diffuser 50 to the supporting surface.

The base portion 51 is shaped such that there is a channel 90 extending around the block receiving portion 52. This channel collects ash produced from the burning block and reduces the amount of ash spilling onto the surface supporting the device 50.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A diffuser for enabling diffusion of vapor or smoke produced from a burning solid block containing an additive, the diffuser comprising:
    a base portion having a first top surface and a first undersurface; and
    a block receiving portion having a second top surface and a second undersurface, the block receiving portion being elevated relative to the first top surface of the base portion to form a platform having a shape to receive the block, and the block receiving portion having at least one groove on the second top surface.

2. The diffuser according to claim 1, wherein the second undersurface of the block receiving portion is elevated relative to the first undersurface of the base portion.

3. The diffuser according to claim 1, wherein the base portion has a spacer formed on the first undersurface, the spacer serving to prevent the second undersurface of the block receiving portion from coming into contact with a surface for supporting the diffuser in use.

4. The diffuser according to claim 1, wherein the block receiving portion is positioned within a depressed portion of the base portion.

5. The diffuser according to claim 1, further comprising a lid portion adapted to fit over the base portion.

6. The diffuser according to claim 5, wherein the lid portion is substantially pyramidal in shape, having an apex positioned at an end remote from the base portion.

7. The diffuser according to claim 5, wherein the lid portion has at least one aperture positioned proximate an apex of the lid portion, which apertures serve in use to enhance a flow of air and vapor within the diffuser.

8. The diffuser according to claim 7, wherein the apertures have a diameter of at least 5 mm.

9. The diffuser according to claim 1, further comprising a combustible solid block containing an additive and positioned on the block receiving portion.

10. The diffuser according to claim 1, wherein the at least one groove on the second top surface is located such that, when the block is positioned on the platform, the at least one groove forms a channel underneath the block to allow a flow of air to an undersurface of the block.

11. The diffuser according to claim 10, having two of the grooves.

12. The diffuser according to claim 11, wherein the two grooves intersect one another.

13. The diffuser according to claim 10, wherein the second top surface is substantially horizontal.

14. The diffuser according to claim 13, wherein the second top surface is substantially flat.

\* \* \* \* \*